US012270020B2

United States Patent
Sumaru et al.

(10) Patent No.: US 12,270,020 B2
(45) Date of Patent: Apr. 8, 2025

(54) CELL CULTURE INSTRUMENT AND CELL PROCESSING METHOD

(71) Applicants: National Institute of Advanced Industrial Science and Technology, Tokyo (JP); KATAOKA CORPORATION, Kyoto (JP)

(72) Inventors: Kimio Sumaru, Ibaraki (JP); Toshiyuki Takagi, Ibaraki (JP); Toshiyuki Kanamori, Ibaraki (JP); Kana Morishita, Ibaraki (JP); Junichi Matsumoto, Kyoto (JP)

(73) Assignees: National Institute of Advanced Industrial Science and Technology, Tokyo (JP); Kataoka Corporation, Kyoto (JP)

( * ) Notice: Subject to any disclaimer, the term of this patent is extended or adjusted under 35 U.S.C. 154(b) by 973 days.

(21) Appl. No.: 17/312,620

(22) PCT Filed: Dec. 13, 2019

(86) PCT No.: PCT/JP2019/048865
§ 371 (c)(1),
(2) Date: Jun. 10, 2021

(87) PCT Pub. No.: WO2020/122225
PCT Pub. Date: Jun. 18, 2020

(65) Prior Publication Data
US 2022/0073862 A1    Mar. 10, 2022

(30) Foreign Application Priority Data
Dec. 13, 2018   (JP) .................................. 2018-233382

(51) Int. Cl.
C12M 1/00     (2006.01)
C12M 1/12     (2006.01)
(Continued)

(52) U.S. Cl.
CPC ............ *C12M 47/02* (2013.01); *C12M 23/20* (2013.01); *C12M 25/00* (2013.01); *C12M 33/00* (2013.01);
(Continued)

(58) Field of Classification Search
None
See application file for complete search history.

(56) References Cited

U.S. PATENT DOCUMENTS 10,876,086 B2 * 12/2020 Suzuki ................. C12N 5/0081
11,441,113 B2 *  9/2022 Matsumoto ............ C12N 13/00
(Continued)

FOREIGN PATENT DOCUMENTS

CN      103570872 A  *  2/2014
EP      3 305 888 A1    4/2018
(Continued)

OTHER PUBLICATIONS

Extended European Search Report dated Dec. 17, 2021 received in 19894692.3.
(Continued)

*Primary Examiner* — Sanza L. McClendon
(74) *Attorney, Agent, or Firm* — Scully, Scott, Murphy & Presser, P.C.

(57) ABSTRACT

A cell culture instrument configured to detach cells at a desired position and a cell processing method using the cell culture instrument. The cell culture instrument includes: a substrate; and a photoreactive layer having a photosolubility and a photothermal convertibility, wherein the photoreactive layer is laminated on the substrate, and the photoreactive layer includes a polymer having a photosolubility and a photothermal convertibility.

18 Claims, 9 Drawing Sheets

(51) Int. Cl.
*C12M 1/26* (2006.01)
*C12N 5/071* (2010.01)
(52) U.S. Cl.
CPC ........ *C12N 5/0602* (2013.01); *C12N 2509/00* (2013.01); *C12N 2533/30* (2013.01)

(56) References Cited

U.S. PATENT DOCUMENTS

| | | | | |
|---|---|---|---|---|
| 11,504,810 | B2 * | 11/2022 | Suzuki | C12N 1/00 |
| 11,566,093 | B2 * | 1/2023 | Sumaru | C08F 220/14 |
| 12,018,239 | B2 * | 6/2024 | Suzuki | C12M 23/20 |
| 2003/0219889 | A1 * | 11/2003 | Sumaru | C12M 47/04 435/287.1 |
| 2013/0023025 | A1 | 1/2013 | Sumaru et al. | |
| 2018/0142193 | A1 | 5/2018 | Suzuki et al. | |
| 2018/0201890 | A1 | 7/2018 | Higuchi et al. | |
| 2020/0317839 | A1 | 10/2020 | Sumaru et al. | |
| 2021/0340482 | A1 * | 11/2021 | Matsumoto | C12M 25/18 |
| 2022/0073862 | A1 * | 3/2022 | Sumaru | C08F 220/54 |

FOREIGN PATENT DOCUMENTS

| | | | | |
|---|---|---|---|---|
| JP | 2003-155357 | A | | 5/2003 |
| JP | 5396803 | B2 | | 1/2014 |
| JP | 5879942 | B2 * | | 3/2016 |
| JP | 6090891 | B1 | | 3/2017 |
| WO | 2011/125615 | A1 | | 10/2011 |
| WO | 2016/194454 | A1 | | 12/2016 |
| WO | 2017/010100 | A1 | | 1/2017 |
| WO | 2017/213226 | A1 | | 12/2017 |
| WO | WO-2019035436 | A1 * | 2/2019 | ............. C12M 1/00 |
| WO | WO-2020071332 | A1 * | 4/2020 | ............ C12M 23/10 |

OTHER PUBLICATIONS

Negrell C. et al., "From monomer synthesis to polymers with pendant aldehyde groups", European Polymer Journal, 2018, vol. 109, pp. 544-563.

International Search Report dated Mar. 17, 2020 issued in PCT/JP2019/048865.

Sumaru K. et.al., "Photo-manipulation of Cultured Cell Monolayer Using PAG Polymer Thin Layer", Membrane, 2015, vol. 40, No. 3, pp. 130-136, cited in ISR.

Sumaru K. et.al., "Photoresponsive Aqueous Dissolution of Poly(N-Isopropylacrylamide) Functionalized with o-Nitrobenzaldehyde through Phase Transition", Biomacromlecules, 2018, vol. 19, pp. 2913-2922, cited in ISR.

* cited by examiner

CELL CULTURE INSTRUMENT AND CELL PROCESSING METHOD

CROSS-REFERENCE TO RELATED APPLICATIONS

The present application is based upon and claims the benefit of priority from PCT/JP2019/048865 filed on Dec. 13, 2019, which claims benefit to JP 2018-233382 filed on Dec. 13, 2018, the entire disclosure of each of which are incorporated herein in their entirety by reference.

BACKGROUND

Field

The present disclosure relates to a cell culture instrument and a cell processing method.

Prior Art

In the case of recovering adherent cells cultured on a cell culture instrument such as a dish or the like, adhesion between the cells and the culture instrument is cut in the presence of a protease such as trypsin and a chelating agent such as EDTA, and released cells are detached and recovered (see WO2017/010100).

However, cells on the entire surface of the culture instrument can be recovered by the method using a protease, but the working position of the protease cannot be limited so that the cells at the desired position cannot be detached and recovered.

Further, when the cells are cultured on a culture instrument, the cells adhere to one another to form a cell mass such as a sheet. In this case as well, cells on the entire surface of the culture instrument can be recovered by the method using a protease, but the working position of the protease cannot be limited so that the cells at the desired position cannot be recovered.

SUMMARY

With the foregoing in mind, it is an object to provide a cell culture instrument configured to detach cells at a desired position and a cell processing method using the cell culture instrument.

In order to achieve the above object, a cell culture instrument (hereinafter, also referred to as a "culture instrument") is provided, the cell culture instrument including: a substrate; and a photoreactive layer having a photosolubility and a photothermal convertibility, wherein the photoreactive layer is laminated on the substrate, and the photoreactive layer includes a polymer having a photosolubility and a photothermal convertibility.

Also provided is a cell processing method (hereinafter, also referred to as a "processing method"), including: a culturing step of culturing cells in the cell culture instrument; a first irradiation step of irradiating the photoreactive layer with first light that causes photodissolution; and a second irradiation step of irradiating the photoreactive layer with second light that causes photothermal conversion.

Accordingly, cells at a desired position can be detached.

BRIEF DESCRIPTION OF DRAWINGS

FIG. 1A is a schematic perspective view of a culture instrument of the first embodiment, FIG. 1B is a schematic cross-sectional view of the culture instrument of the first embodiment taken along line I-I of FIG. 1A, and FIG. 1C is a schematic cross-sectional view of a culture instrument 100 taken along line I-I of FIG. 1A in a state where cells are cultured in the culture instrument 100.

FIG. 3A is a schematic perspective view of a culture instrument of the second embodiment, FIG. 3B is a schematic cross-sectional view of the culture instrument of the second embodiment taken along line II-II of FIG. 3A, and FIG. 3C is a schematic cross-sectional view of a culture instrument 200 taken along line II-II of FIG. 3A in a state where cells are cultured in the culture instrument 200.

FIG. 5A shows a region of cells to be processed in a culture instrument, and FIG. 5B is a photograph showing the result of the culture instrument after processing by a processing method.

FIG. 6A shows a region of cells to be processed in a culture instrument, and FIG. 6B is a photograph showing the result of the culture instrument after processing by a processing method.

FIG. 7A shows a region of cells to be processed in a culture instrument, and FIG. 7B is a photograph showing the result of the culture instrument after processing by a processing method.

FIG. 8A shows a region of cells to be processed in a culture instrument, and FIG. 8B is a photograph showing the result of the culture instrument after processing by a processing method.

FIG. 9A shows a region of cells to be processed in a culture instrument, and FIG. 9B is a photograph showing the result of the culture instrument after processing by a processing method.

DETAILED DESCRIPTION

In the present disclosure, "cells" mean, for example, isolated cells, cell masses composed of cells, tissues, or organs. The cells may be, for example, cultured cells or cells isolated from a living body. In addition, the cell mass, tissue, or organ may be, for example, a cell mass, a cell sheet, a tissue, or an organ made from the cells, or a cell mass, a tissue, or an organ isolated from a living body.

In the present disclosure, "cell processing" may be used in any sense of, for example, detachment of cells, recovery of cells, removal of unnecessary cells, and retention or maintenance of necessary cells.

Hereinafter, a cell culture instrument and a cell processing method will be described in detail with reference to the drawings. The present invention, however, is not limited to the following description. In the following FIGS. 1A to 9B, identical parts are indicated with identical reference signs, and the descriptions of the identical parts may be omitted. Furthermore, for convenience in explanation, the structure of each component shown in FIGS. 1A to 9B may be appropriately simplified, and the size, the ratio, and the like of components may be schematically shown and different from actual ones. Each embodiment can be described with reference to the descriptions of other embodiments, unless otherwise specified.

First Embodiment

Figure 1A:
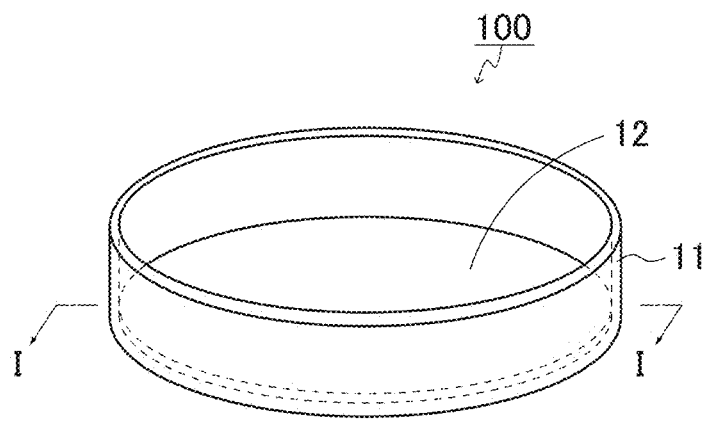
FIGS. 1A to 1C are schematic views showing an example of the configuration of a culture instrument of the first embodiment.
Figure 1B:
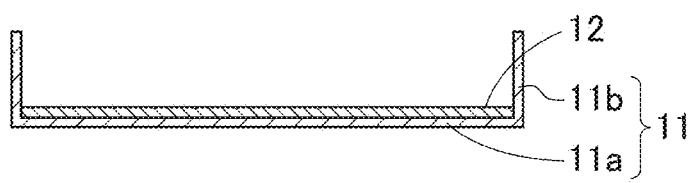
Figure 1C:
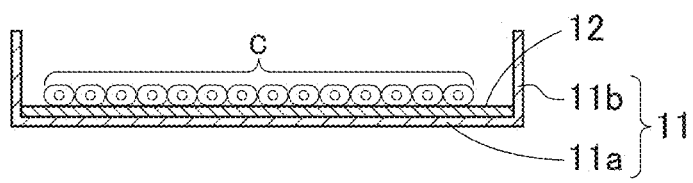

The present embodiment is an example of a cell culture instrument and a cell processing method. FIGS. 1A to 1C are schematic views showing the configuration of a culture instrument 100 of the first embodiment. FIG. 1A is a schematic perspective view of the culture instrument 100, FIG. 1B is a schematic cross-sectional view of the culture instrument 100 taken along line I-I of FIG. 1A, and FIG. 1C is a schematic cross-sectional view of the culture instrument 100 taken along line I-I of FIG. 1A in a state where cells are cultured in the culture instrument 100. As shown in FIGS. 1A and 1B, the culture instrument 100 includes a container 11 and a photoreactive layer 12. The container 11 has a circular substrate 11a and a side wall 11b surrounding the outer periphery of the substrate 11a. The photoreactive layer 12 includes a polymer having a photosolubility and a photothermal convertibility (hereinafter, also referred to as a "photoreactive polymer"). The photoreactive layer 12 is laminated on the substrate 11a. Further, as shown in FIG. 1C, cells C are cultured on the photoreactive layer 12 in the culture instrument 100, that is, the cells C are cultured in a region surrounded by the photoreactive layer 12 and the side wall 11b. The cells C may be in contact with the photoreactive layer 12 as shown in FIG. 1C or may be in contact with the photoreactive layer 12 via another layer or the like. In FIG. 1C, a medium is not shown (the same applies hereinafter).

The container 11 is configured to culture the cells. In the container 11, a space surrounded by the substrate 11a and the side wall 11b is a region (cell culture region) configured to culture the cells. The container 11 may be a cell culture container, and specific examples thereof include a dish, a plate, and a flask (cell culture flask). The size, shape, volume, material, whether an adhesion processing has been performed, and the like of the container 11 can be appropriately determined according to the type and amount of cells to be cultured in the culture instrument 100. While the container 11 has the side wall 11b in the culture instrument 100, the side wall 11b is an optional component and the container 11 may or may not have the side wall 11b. Examples of the container 11 without the side wall 11b include the plates and preparations. The substrate 11a may be a planar substrate or a substrate with irregularities.

The material of the container 11 and the substrate 11a and the side wall 11b that comprise the container 11 may be the same or different. A material used for a cell culture container can be used as the material, for example, and the material can be a translucent material. Examples of the material include plastics such as polystyrene, polymethylpentene, polycarbonate, cycloolefin polymers, and the like; glass; quartz; silicone resins; and cellulosic materials.

While the container 11 has one cell culture region, the container 11 may have a plurality of cell culture regions. In the latter case, it can also be said that the container 11 has a plurality of wells, for example. In addition, in the latter case, the photoreaction region 12 may be formed in any one of the plurality of cell culture regions, the photoreactive layers 12 may be formed in some of the plurality of cell culture regions, or the photoreactive layers 12 may be formed in all of the plurality of cell culture regions. In other words, the photoreactive layer(s) 12 may be formed in any one of, two or more of, or all of the plurality of wells of the container 11.

While the photoreactive layer 12 is laminated on the entire surface of the substrate 11a in the present embodiment, the photoreactive layer 12 may be laminated on a part of the substrate 11a. When the photoreactive layer 12 is laminated on a part of the substrate 11a, the size and shape thereof can be set to a desired size and shape. The photoreactive layer 12 may be formed so as to correspond to, for example, the size and shape of the cells desired to be detached.

In the present embodiment, the container 11 may include a lid. The lid may removably cover, for example, the upper surface of the container 11. The lid is disposed so as to face the substrate 11a, for example. Examples of the lid include a lid, a cap, and the like of the cell culture container.

The photoreactive layer 12 includes the photoreactive polymer as described above. The photoreactive polymer is dispersed in a part or the entire of the photoreactive layer 12, and the photoreactive polymer can be dispersed in the entire of the photoreactive layer 12. The photoreactive layer 12 may include, as the polymer having a photosolubility and a photothermal convertibility, a polymer having a photothermal convertibility and a polymer having a photosolubility, or a polymer having both of a photosolubility and a photothermal convertibility, for example. Next, each polymer will be described.

(1) Photosoluble Polymer

The photosoluble polymer is, for example, a polymer whose solvent solubility is changed by light irradiation, and is, for example, a polymer whose solubility in an aqueous solvent (e.g., water, a medium, or the like) is greatly changed by light irradiation. Therefore, in the case where the photoreactive layer 12 includes the photosoluble polymer, when the cells C are cultured on the photoreactive layer 12 as shown in FIG. 1C, indirect fixation (adhesion) of the cells C to the substrate 11a can be released by dissolving the photoreactive layer 12 in a solvent by light irradiation.

The photosoluble polymer has a main chain and a side chain, the side chain has an aromatic ring, the aromatic ring includes a first carbon atom substituted with a nitro group and a second carbon atom substituted with an aldehyde group or a functional group represented by the following formula (1), and the first carbon atom and the second carbon atom are adjacent to each other within the same benzene ring, for example. By using such a polymer, the solubility in an aqueous solvent can be greatly changed by the light irradiation, and the photosolubility can be suitably exhibited.

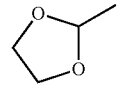

(1)

The main chain can also be referred to as, for example, a skeleton constituting a polymer. Examples of the skeleton constituting the polymer include an acrylic polymer such as an acrylamide polymer, a polystyrene polymer, a polyolefin polymer, polyvinyl acetate, polyvinyl chloride, a polyolefin polymer, a polycarbonate polymer, and an epoxy polymer.

The aromatic ring may be, for example, an aromatic hydrocarbon or a heteroaromatic compound. Examples of the aromatic ring include a benzene ring, a naphthalene ring, an anthracene ring, and a naphthacene ring. The aromatic ring is bonded directly or indirectly to the main chain (A, described below), for example. In the direct bond, the aromatic ring is directly bonded to the main chain in a single bond. The indirect bond may be a bond via an ester bond, an ether bond, an amide bond, a thioether bond, a thioester bond, a urethane bond, or an alkylene group, or may be a bond via an ester bond, an ether bond, an amide bond, a thioether bond, a thioester bond, a urethane bond, or another functional group having an alkylene group, for example.

The photosoluble polymer can include a polymer represented by the following formula (2):

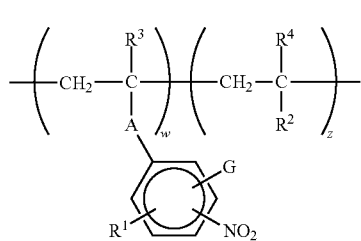

(2)

In the formula (2), A is a single bond or a functional group, $R^1$ is an aldehyde group or a functional group represented by the formula (1), $R^1$ and $NO_2$ are each attached to adjacent carbon atoms, $R^2$ is at least one selected from the group consisting of hydrogen atoms, alkyl groups, functional groups represented by the following formula (3), and functional groups represented by the following formula (4), $R^3$ and $R^4$ may be the same or different and are each independently a hydrogen atom or an alkyl group, G is three or less alkyl groups which may be substituted with hydrogen in a benzene ring, and w and z represent mole percentages and satisfy $0<w\leq100$ and $0\leq z<100$,

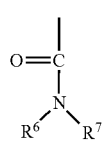

(3)

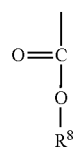

(4)

In the formula (3), $R^6$ and $R^7$ may be the same or different and are each independently a hydrogen atom, an alkyl group, or an aromatic ring. In the formula (4), $R^8$ is an alkyl group.

The alkyl group can be a straight-chain, branched, or cyclic alkyl group containing one to six carbon atoms, for example. Specific examples of the alkyl group include a methyl group, an ethyl group, a propyl group, an iso-propyl group, a butyl group, a tert-butyl group, a sec-butyl group, an iso-butyl group, a pentyl group, a neopentyl group, an isopentyl group, a sec-pentyl group, a tert-pentyl group, a cyclopentyl group, and a hexyl group.

The structure of A that links the main chain and the benzene ring is not restricted, and may be, for example, a single bond, an ester bond, an ether bond, an amide bond, a thioether bond, a thioester bond, a urethane bond, or a functional group having an alkylene group. That is, the main chain and the benzene ring may be directly bonded in a single bond, or may be bonded via an ester bond, an ether bond, an amide bond, a thioether bond, a thioester bond, a urethane bond, or an alkylene group, or may be bonded via an ester bond, an ether bond, an amide bond, a thioether bond, a thioester bond, a urethane bond, or another functional group having an alkylene group.

The photosoluble polymer can include a polymer represented by the following formula (5). In the following formula (5), monomers may be randomly polymerized or may be polymerized with regularity.

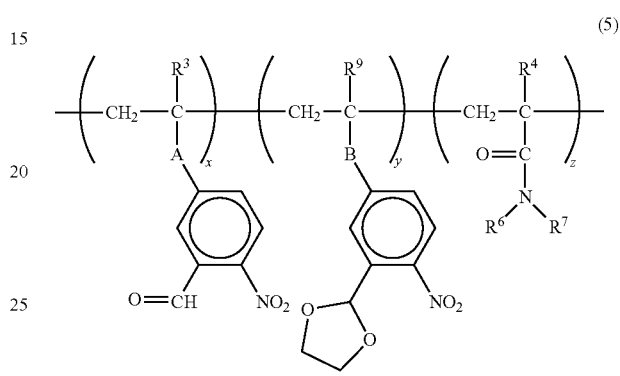

(5)

In the formula (5), A and B may be the same or different and are each independently a single bond or a functional group, $R^3$, $R^4$, and $R^9$ may be the same or different and are each independently a hydrogen atom or an alkyl group, $R^6$ and $R^7$ may be the same or different and are each independently a hydrogen atom, an alkyl group, or an aromatic ring, and x, y, and z represent mole percentages and satisfy $0\leq x<100$, $0\leq y<100$, and $0\leq z<100$ (except for $x=y=0$), respectively.

When $R^6$ and $R^7$ are each an alkyl group, $R^6$ and $R^7$ can each be an iso-propyl group or a tert-butyl group.

x and y can satisfy $x>y$ so that cells can be processed more efficiently, for example. As to x, y, and z, $x/(x+y+z)$ can be 0.04 or more.

Examples of the polymers represented by the formula (2) or (5) include polymers represented by the formula (11) or (12) to be described below.

Regarding the structures of A and B that link the main chain and the benzene ring, reference can be made to the description as to the structure of A that links the main chain and the benzene ring. The side chain linked by A can be generated, for example, by hydrolyzing an acetal group of the side chain linked by B. Therefore, the structures of A and B that link the main chain and the benzene ring can be the same.

Regarding the method for producing the photosoluble polymer, for example, reference can be made to the description of WO 2017/013226, which is incorporated herein by reference.

(2) Photothermal Convertible Polymer

The photothermal convertible polymer is a polymer which generates heat by light irradiation. Thus, in the case where the photoreactive layer 12 includes the photothermal convertible polymer, when the cells C are cultured on the photoreactive layer 12 as shown in FIG. 1C, heat is generated in the photoreactive layer 12 by light irradiation, thereby killing the cell(s) C adjacent to the photoreactive layer 12 irradiated with light, i.e., the cell(s) C directly above the light irradiated part. As a result, it is possible to release the fixation (adhesion) between the cells C that are indirectly adhered via the killed cell C.

The photothermal convertible polymer is, for example, a polymer having a chromophore that absorbs a wavelength of light to be irradiated. The photothermal convertible polymer has, for example, a main chain and a side chain, and the side chain has the chromophore. Examples of the chromophore include a compound having an azobenzene skeleton or a derivative thereof and derivatives of organic compounds such as diaryleton, spiropyran, spirooxazine, flugid, leuco dye, indigo, carotenoid (carotene, etc.), flavonoid (anthocyanin, etc.), quinoid (anthraquinone, etc.), and the like.

The main chain can also be referred to as, for example, a skeleton constituting a polymer. Examples of the skeleton constituting the polymer include an acrylic polymer such as an acrylamide polymer, a polystyrene polymer, a polyolefin polymer, polyvinyl acetate, polyvinyl chloride, a polyolefin polymer, a polycarbonate polymer, and an epoxy polymer.

The side chain can have a chromophore having a predetermined absorbance at a wavelength of 350 nm or more. The predetermined absorbance is, for example, 0.01 or more, such as 0.1 or more. The side chain can have an absorbance of 0.01 or more, such as 0.1 or more, in a wavelength range of 350 nm or more and 1300 nm or less, for example. The absorbance can be measured using an absorbance meter. Examples of the chromophore having the predetermined absorbance include tar dyes such as an azo dye (e.g., dye having an azobenzene skeleton), a fluorescein dye, a leuco dye, a phenol dye, a polycyclic aromatic dye, indigoid, and the like; and dyes having a natural dye skeleton such as carotenoid, flavonoid, a polyphyllin dye, an anthocyanin dye, an alizarin dye, a phycobilin dye, a quinone dye, and the like. Specific examples of the chromophore having the predetermined absorbance include Disperse Yellow 7 and Disperse Orange 3,4-(4-nitrophenylazo) phenol.

The chromophore is bonded directly or indirectly to the main chain, for example. In the direct bond, the aromatic ring is directly bonded to the main chain in a single bond. The indirect bond may be a bond via an ester bond, an ether bond, an amide bond, a thioether bond, a thioester bond, a urethane bond, or an alkylene group, or may be a bond via an ester bond, an ether bond, an amide bond, a thioether bond, a thioester bond, a urethane bond, or another functional group having an alkylene group, for example.

Specific examples of the photothermal convertible polymer include polymers represented by the following formulae (8) to (10).

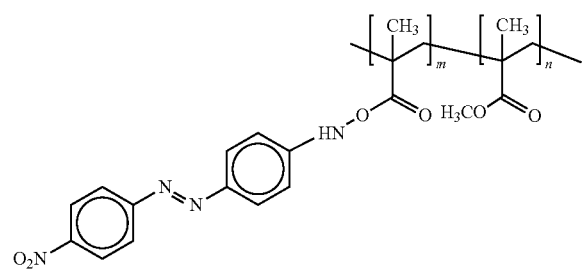

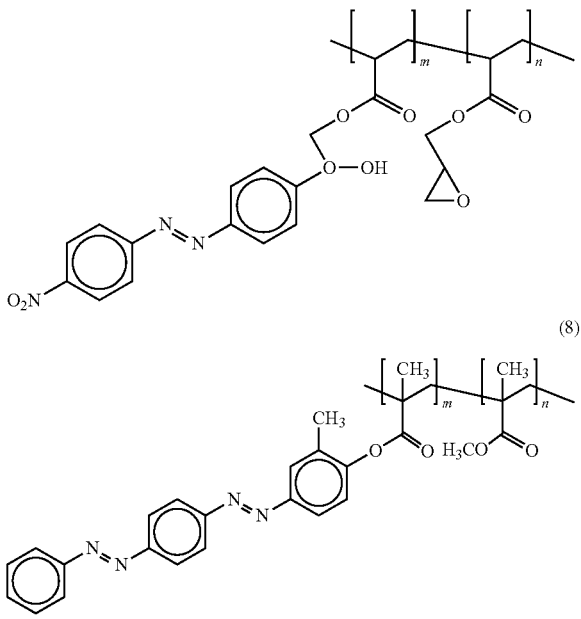

In the formulae (8) to (10), m and n represent mole percentages and satisfy $0<m\leq100$ and $0\leq n<100$, respectively. In the formulae (8) to (10), the structure of azobenzene in the polymer may employ, besides an unsubstituted azobenzene, various variations of the structure modified with a nitro group, an amino group, a methyl group, or the like.

The photothermal convertible polymer may be produced, for example, by reacting a functional group of a main chain constituting a photothermal convertible polymer with a functional group of the chromophore. Furthermore, the photothermal convertible polymer may be produced, for example, by polymerizing a monomer having a chromophore obtained by reacting a functional group of a monomer of the main chain with a functional group of the chromophore with a monomer of the main chain.

(3) Photosoluble and Photothermal Conversible Polymer

The photosoluble and photothermal convertible polymer is a polymer having both characteristics of a photosoluble polymer and a photothermal convertible polymer. In the photosoluble and photothermal convertible polymer, an atomic group responsible for a photosolubility and an atomic group responsible for a photothermal convertibility exhibit their characteristics by light having different characteristics, for example. Specifically, for example, the atomic group responsible for a photosolubility and the atomic group responsible for a photothermal convertibility exhibit their characteristics by light of different energies (light irradiation amounts), and the atomic group responsible for a photothermal convertibility exhibits its characteristic by light of high energy as compared to the atomic group responsible for a photosolubility. Thus, by irradiating the photoreactive layer 12 with light by which each atomic group exhibits its characteristic, it is possible to release the indirect fixation between the cells C and the substrate 11a due to the dissolution of the photosoluble and photothermal convertible polymer in the photoreactive layer 12 and to release the fixation between the cells C indirectly adhered via the killed cell(s) C due to the killing of the cell(s) C.

The photosoluble and photothermal convertible polymer has a main chain and a side chain, the side chain has a first side chain and a second side chain, the first side chain is a side chain of the photosoluble polymer and the second side chain is a side chain of the photothermal convertible polymer, for example. Regarding the description of the side chain of the photosoluble polymer and the side chain of the photothermal convertible polymer, reference can be made to the above-described description.

The photosoluble and photothermal convertible polymer can include a polymer represented by the following formula (6). In the formula (6), monomers may be randomly polymerized or may be polymerized with regularity.

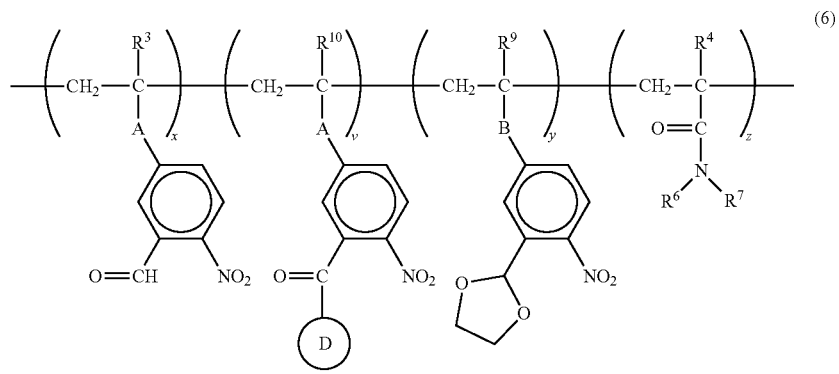

(6)

In the formula (6), A and B may be the same or different and are each independently a single bond or a functional group, $R^3$, $R^4$, $R^9$, and $R^{10}$ may be the same or different and are each independently a hydrogen atom or an alkyl group, $R^6$ and $R^7$ may be the same or different and are each independently a hydrogen atom, an alkyl group, or an aromatic ring, D is a chromophore having a predetermined absorbance at a wavelength of 350 nm or more, and v, x, y, and z represent mole percentages and satisfy $0<v<100$, $0 \le x<100$, $0 \le y<100$, and $0 \le z<100$ (except for $x=y=0$), respectively.

Examples of the polymers represented by the formula (6) include polymers represented by the formula (13) to be described below.

The photosoluble and photothermal convertible polymer can include a polymer represented by the following formula (7). In the following formula (7), monomers may be randomly polymerized or may be polymerized with regularity.

In the formula (7), A, B, and E may be the same or different and are each independently a single bond or a functional group, $R^3$, $R^4$, $R^9$, and $R^{11}$ may be the same or different and are each independently a hydrogen atom or an alkyl group, $R^6$ and $R^7$ may be the same or different and are each independently a hydrogen atom, an alkyl group, or an aromatic ring, D is a chromophore having a predetermined absorbance at a wavelength of 350 nm or more, and u, x, y, and z represent mole percentages and satisfy $0<u<100$, $0 \le x<100$, $0 \le y<100$, and $0 \le z<100$ (except for $x=y=0$), respectively.

Regarding the description of A, B, and substituents in the formulae (6) and (7), reference can be made to the descriptions as to the "(1) photosoluble polymer" and "(2) photothermal convertible polymer".

The structure of E that links the main chain and a chromophore having a predetermined absorbance is not particularly restricted, and may be, for example, a single bond, an ester bond, an ether bond, an amide bond, a thioether bond, a thioester bond, a urethane bond, or a functional group having an alkylene group. That is, the main chain and the benzene ring may be directly bonded in a single bond, or may be bonded via an ester bond, an ether bond, an amide bond, a thioether bond, a thioester bond, a urethane bond, or an alkylene group, or may be bonded via an ester bond, an ether bond, an amide bond, a thioether bond, a thioester bond, a urethane bond, or another functional group having an alkylene group.

The photosoluble and photothermal convertible polymer may be produced, for example, by reacting an aldehyde group of the photosoluble polymer with a functional group

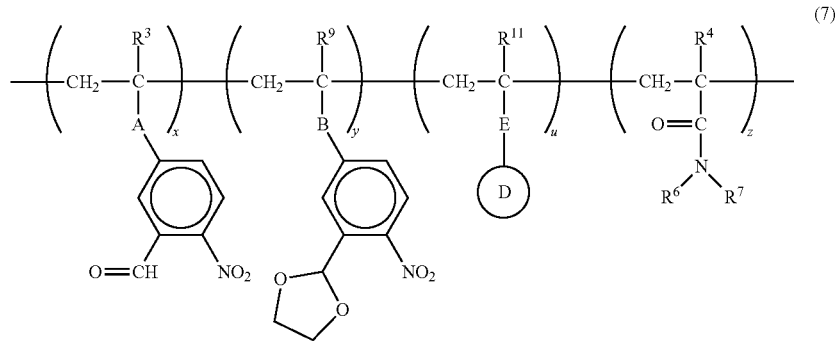

(7)

of the chromophore, or may be produced by polymerizing each monomer of the photosoluble polymer, a monomer of the main chain into which the chromophore is introduced, and a monomer of the main chain.

The photoreactive layer 12 may include other components besides the photoreactive polymer. Examples of the other components include photomeltable materials. The photomeltable material means, for example, a photoresponsive material configured to induce solidification and liquefaction by light of different wavelengths.

A method for producing the culture instrument 100 of the present embodiment includes, for example, a photoreactive layer forming step of forming the photoreactive layer 12 on the substrate 11a. The photoreactive layer 12 may be formed by, for example, a known film forming method, and specific examples of the method include a coating method, a printing method (screen method), a vapor deposition method, a sputtering method, a casting method, and a spin coating method. When the photoreactive polymer in the photoreactive layer 12 includes the photosoluble polymer and the photothermal convertible polymer, the photoreactive layer 12 can be formed by mixing the photosoluble polymer and the photothermal convertible polymer and using the obtained mixture. When the photosoluble polymer and the photothermal convertible polymer are dispersed in a solvent, the method for producing the culture instrument 100 can include a step of removing the solvent after forming the photoreactive layer 12 on the substrate 11a. In the manner as described above, the culture instrument 100 of the present embodiment can be produced.

The culture instrument 100 of the present embodiment may include, for example, a connection layer connecting the photoreactive layer 12 and the substrate 11a. In this case, the connection layer is laminated on the substrate 11a and the photoreactive layer 12 is laminated on the connection layer, i.e., the connection layer is disposed between the substrate 11a and the photoreactive layer 12. By including the connection layer, the culture instrument 100 can maintain the responsiveness of the photoreactive layer 12 even when long-term cell culture is performed so that the cells C can be excellently detached even after long-term culture, for example.

The connection layer includes, for example, a polymer having high hydration characteristic and rich in hydroxyl groups. As a specific example, the connection layer includes, for example, a crosslinked product of a cellulose derivative such as hydroxypropyl cellulose, hydroxybutyl cellulose, or the like, poly(hydroxyethyl methacrylate) and its copolymer. The crosslinked product of the cellulose derivative may be, for example, a product obtained by crosslinking hydroxypropyl cellulose with poly(ethylene glycol)bis(carboxymethyl) ether.

When the culture instrument 100 has the connection layer, the method for producing the culture instrument 100 of the present embodiment can include a step of forming the connection layer on the substrate 11a prior to the photoreactive layer forming step. In the photoreactive layer forming step, the photoreactive layer 12 can be formed on the connection layer. The connection layer can be formed in the same manner as the formation of the photoreactive layer 12, for example.

The culture instrument 100 of the present embodiment may include a cell culture base material layer on the photoreactive layer 12, for example. In other words, the cell culture base material layer may be laminated on the photoreactive layer 12. With such a configuration, the culture instrument 100 can favorably perform indirect fixation of the cells C to the substrate 11a, for example. Examples of the cell culture base material include an extracellular substrate (extracellular matrix) and a substance having a function as a cell scaffold. Examples of the extracellular substrate include elastin; entactin; collagens such as collagen I, collagen II, collagen III, collagen IV, collagen V, collagen VII, and the like; tenascin; fibrillin; fibronectin; laminin; vitronectin; proteoglycan composed of sulfated glucosaminoglycan such as chondroitin sulfate, heparan sulfate, keratan sulfate, dermatan sulfate, or the like and a core protein; glucosaminoglycans such as chondroitin sulfate, heparan sulfate, keratan sulfate, dermatan sulfate, hyaluronic acid, and the like; Synthemax® (vitronectin derivative); and Matrigel® (mixture of laminin, collagen IV, heparin sulfate proteoglycan, entactin/nidogen, and the like). Among them, laminin can be used. The cell culture base material may include a peptide fragment of the protein or a fragment of the sugar chain. As a specific example, the peptide fragment of the protein may be a fragment of laminin Examples of the fragment of laminin include laminin 211-E8, laminin 311-E8, laminin 411-E8, and laminin 511-E8. The laminin 211-E8 is composed of fragments of the $\alpha 2$, $\beta 1$, and $\gamma 1$ chains of laminin. The laminin 311-E8 is composed of fragments of the $\alpha 3$, $\beta 1$, and $\gamma 1$ chains of laminin. The laminin 411-E8 is composed of fragments of the $\alpha 4$, $\beta 1$, and $\gamma 1$ chains of laminin. The laminin 511-E8 is composed of fragments of the $\alpha 5$, $\beta 1$, and $\gamma 1$ chains of laminin, for example.

When the culture instrument 100 includes the cell culture base material layer, the method for producing the culture instrument 100 of the present embodiment can include a step of forming the cell culture base material layer on the photoreactive layer 12 after the photoreactive layer forming step. The cell culture base material layer can be formed in the same manner as the photoreactive layer 12, for example.

Next, a cell processing method using the culture instrument 100 of the present embodiment will be described with reference to FIGS. 2A-2E. FIGS. 2A-2E are schematic views showing an example of a cell processing method using the culture instrument 100. As shown in FIGS. 2A-2E, in the processing method of the present embodiment, by irradiating the culture instrument 100 in which the cultured cells C are present with the first light (L1) and the second light (L2), the desired cells can be detached.

Figure 2A:
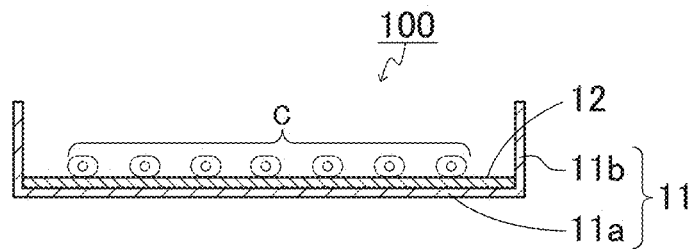
FIGS. 2A-2E are schematic views showing an example of a cell processing method of the first embodiment.
Figure 2B:
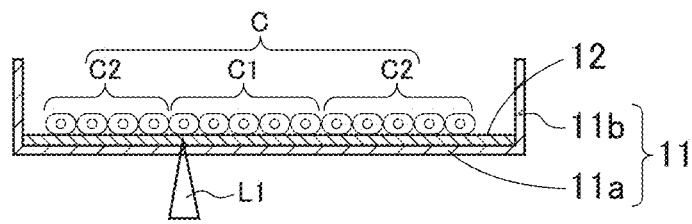

First, in the processing method of the present embodiment, as shown in FIG. 2A and FIG. 2B, cells are cultured in the culture instrument 100 (culturing step). Cells to be cultured can be introduced, for example, by introducing a cell suspension into the culture instrument 100. The culture conditions (culture temperature, culture humidity, gas partial pressure, culture time, and the like) in the culturing step can be appropriately determined according to the type of the cells, for example. Specifically, the culture can be performed in a wet environment at 5% $CO_2$ and 25 to 40° C.

Figure 2C:
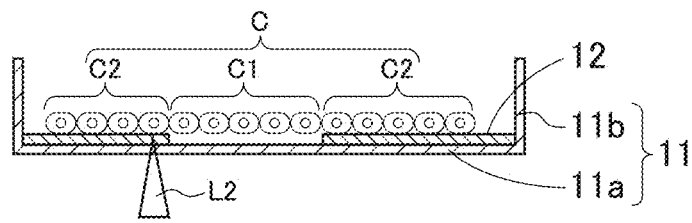

Next, the photoreactive layer 12 is irradiated with first light (L1) that causes photodissolution (first irradiation step). More specifically, in the first irradiation step, the photoreactive layer 12 corresponding to cells C1 to be processed (detached) among cells C is irradiated with L1, that is, the photoreactive layer 12 immediately below the cells C1 to be processed is irradiated with L1. As a result, as shown in FIG. 2C, the photoreactive layer 12 immediately below the cells C1 to be processed is dissolved, and the indirect fixation (adhesion) of the cells C1 to the substrate 11a is released. The wavelength of L1 is a wavelength at which an atomic group responsible for a photosolubility exhibits a photosolubility in the photoreactive polymer. As a specific example, the wavelength of L1 is, for example, 310 to 410 nm, such as 350 to 410 nm or 360 to 370 nm. Further, the light irradiation amount (J/cm$^2$) of L1 can be set as appropriate according to the wavelength of the light to be irradiated with and its energy amount, for example. As a specific example, when the wavelength of L1 is 365 nm, the light irradiation amount is, for example, 0.05 to 1 J/cm$^2$, such as 0.1 to 0.5 J/cm$^2$. In addition, when the wavelength of L1 is 405 nm, the light irradiation amount is, for example, 0.5 to 10 J/cm$^2$, such as 1 to 5 J/cm$^2$. While L1 is laser light, i.e., point light in the present embodiment, L1 is not limited thereto and may be planar light.

Figure 2D:
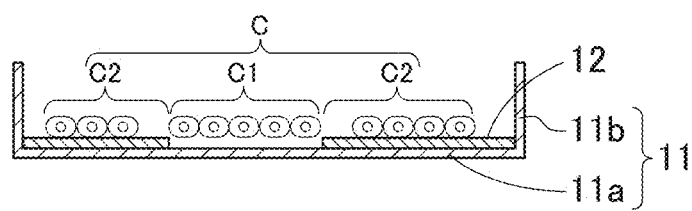
Figure 2E:
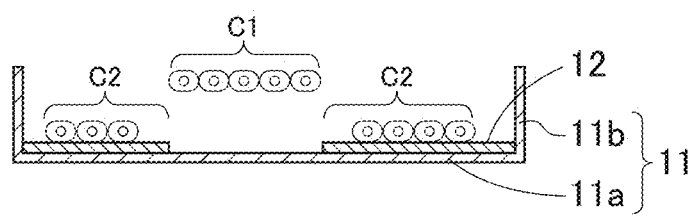

Next, the photoreactive layer 12 is irradiated with second light (L2) that causes photothermal conversion (a second irradiation step). Specifically, in the second irradiation step, the photoreactive layer 12 corresponding to the boundary between the cells C1 to be processed (detached) and the cells C2 not to be processed (detached) is irradiated with L2, that is, the photoreactive layer 12 immediately below the cell C2 adjacent to the cells C1 to be processed among the cells C2 not to be processed is irradiated with L2. The boundary can also be referred to a region adjacent to the outer periphery of the region irradiated with L1, for example. As a result, as shown in FIG. 2D, the cell C2 adjacent to the photoreactive layer 12 irradiated with L2 is killed, and the fixation between the cells C1 to be processed and the cells C2 not to be processed is released. Thus, as shown in FIG. 2E, the cells C1 to be processed become detachable. The killing may be induced upon irradiation with L2 or may be induced after irradiation with L2. The wavelength of L2 is a wavelength at which an atomic group (chromophore) responsible for a photothermal convertibility exhibits a photothermal convertibility in the photoreactive polymer. As a specific example, the wavelength of L2 is, for example, 300 nm or more, such as 300 to 1300 nm, or 350 to 1300 nm. The wavelength of L2 may be the same as or different from the wavelength of L1, for example. Further, the light irradiation condition of L2 is, for example, a light irradiation amount with which the cells C adjacent to the part irradiated with L2 is killed, and the light irradiation condition can be set as appropriate according to the output of L2 to be irradiated with, the irradiation size (spot diameter) of L2, and the absorbance of the photoreactive layer at the irradiation wavelength of L2. As a specific example, when the output of the laser light is 0.6 W, the diameter (spot diameter) is 50 μm, and the absorbance of the photoreactive layer 12 at the irradiation light wavelength (wavelength of the laser light) is 0.25, the scanning speed of the laser light can be set to 10 to 500 mm/sec, such as 50 to 200 mm/sec. The light irradiation condition of L2 may be appropriately changed based on the light irradiation condition. As a specific example, when the output of the laser light is doubled and the diameter of the laser light and the absorbance of the photoreactive layer 12 are the same, the scanning speed of the laser light can be set to, for example, about twice, that is, 20 to 1000 mm/sec. In the second irradiation step, the part irradiated with L2 can be irradiated so as to temporarily or continuously increase the temperature to about 100° C. (e.g., 80 to 120° C.). By setting the light irradiation conditions accordingly, the processing method of the present embodiment can effectively kill cells in the second irradiation step, for example. While L2 is laser light, i.e., point light in the present embodiment, L2 is not limited thereto and may be planar light.

In this manner, the processing method of the present embodiment can detach the cells C1 to be processed.

In the present embodiment, since the second irradiation step is performed after the first irradiation step, the photoreactive layer 12 immediately below the cell C2 adjacent to the cells C1 is irradiated with L2. However, the object to be irradiated with L2 is not limited thereto. In other words, in the processing method of the present embodiment, the first irradiation step may be performed after the second irradiation step, or these steps may be performed in parallel. As a specific example, when irradiation of L1 is performed after irradiation of L2, the photoreactive layer 12 immediately below the cell C2 adjacent to the cells C1 to be processed or the photoreactive layer 12 immediately below the cells C1 adjacent to the cells C2 not to be processed is irradiated with L2 in the second irradiation step, for example. In the first irradiation step, the photoreactive layer 12 immediately below the cells C1 may be irradiated with L1.

While one cell C present at the boundary is killed in the processing method of the present embodiment, a plurality of cells C adjacent to the boundary may be killed. Thereby, the processing method of the present embodiment can effectively prevent, for example, that the cells C1 to be processed remain in the cells C2 not to be processed and that the cells C2 not to be processed are detached together with the cells C1 to be processed.

Second Embodiment

Figure 3A:
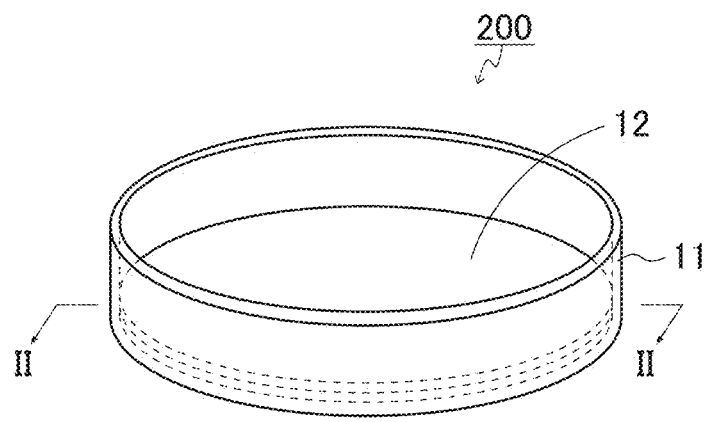
FIGS. 3A to 3C are schematic views showing an example of the configuration of a culture instrument of the second embodiment.
Figure 3B:
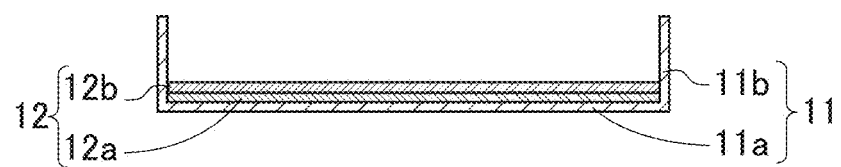
Figure 3C:
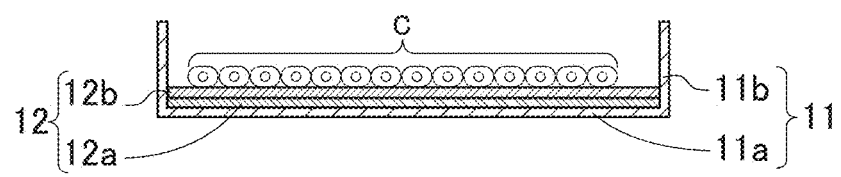

The present embodiment is another example of a cell culture instrument and a cell processing method. FIGS. 3A to 3C are schematic views showing the configuration of a culture instrument 200 of the second embodiment. FIG. 3A is a schematic perspective view of the culture instrument 200, FIG. 3B is a schematic cross-sectional view of the culture instrument 200 taken along line II-II of FIG. 3A, and FIG. 3C is a schematic cross-sectional view of a culture instrument 200 taken along line II-II of FIG. 3A in a state where cells are cultured in the culture instrument 200. As shown in FIGS. 3A to 3C, in the culture instrument 200, the photoreactive layer 12 in the configuration of the culture instrument 100 of the first embodiment is composed of two layers. That is, the photoreactive layer 12 includes a photothermal convertible layer 12a and a photosoluble layer 12b. Further, the photothermal convertible layer 12a is laminated on the substrate 11a, and the photosoluble layer 12b is laminated on the photothermal convertible layer 12a. The cells C may be in contact with the photosoluble layer 12b as shown in FIG. 3C or may be in contact with the photosoluble layer 12b via another layer or the like. Except for this point, the configuration of the culture instrument 200 of the second embodiment is the same as that of the culture instrument 100 of the first embodiment, and reference can be made to the description thereof.

The photothermal convertible layer 12a is a layer having a photothermal convertibility. That is, the photothermal convertible layer 12a is a layer that generates heat by irradiation with light. The photothermal convertible layer 12a includes the aforementioned photothermal convertible polymer. Regarding the photothermal convertible polymer, reference can be made to the description of "(2) photothermal convertible polymer" in the first embodiment. The photothermal convertible layer 12a is formed on a part or the entire of the surface of the substrate 11a, for example.

The photosoluble layer 12b is a layer having a photosolubility. In other words, the photosoluble layer 12b is a layer whose solvent solubility is changed by light irradiation. The photosoluble layer 12b includes the aforementioned photosoluble polymer. Regarding the photosoluble polymer, reference can be made to the description of "(1) photosoluble polymer" in the first embodiment.

While the photosoluble layer 12b is laminated on the photothermal convertible layer 12a in the culture instrument 200, the order of laminating the photothermal convertible layer 12a and the photothermal dissolve layer 12b in the culture instrument 200 is not limited thereto, and the photothermal convertible layer 12a may be laminated on the photosoluble layer 12b. For example, by laminating the photosoluble layer 12b on the photothermal convertible layer 12a, the culture instrument 200 can easily detach the cells to be processed after the first irradiation step and the second irradiation step described below.

The culture instrument 200 may include at least one of the aforementioned connection layer and cell culture base material layer, for example. When the culture instrument 200 includes the connection layer, the connection layer is laminated on the substrate 11a, and the photothermal convertible layer 12a is laminated on the connection layer. When the culture instrument 200 includes the cell culture base material layer, the cell culture base material layer is laminated on the photosoluble layer 12b.

The method for producing the culture instrument 200 of the present embodiment includes, for example, a photothermal convertible layer forming step of forming the photothermal convertible layer 12a on the substrate 11a, and a photosoluble layer forming step of forming the photosoluble layer 12b on the photothermal convertible layer 12a. The photothermal convertible layer 12a and the photosoluble layer 12b can be formed by, for example, a known film forming method, and reference can be made to the description of the method for forming the photoreactive layer 12 in the first embodiment. In the manner as described above, the culture instrument 200 of the present embodiment can be produced.

Next, a cell processing method using the culture instrument 200 of the present embodiment will be described with reference to FIGS. 4A-4E. FIGS. 4A-4E are schematic views showing an example of a cell processing method using the culture instrument 200. As shown in FIGS. 4A-4E, in the processing method of the present embodiment, by irradiating the culture instrument 200 in which the cultured cells C are present with the first light (L1) and the second light (L2), the desired cells can be detached.

Figure 4A:
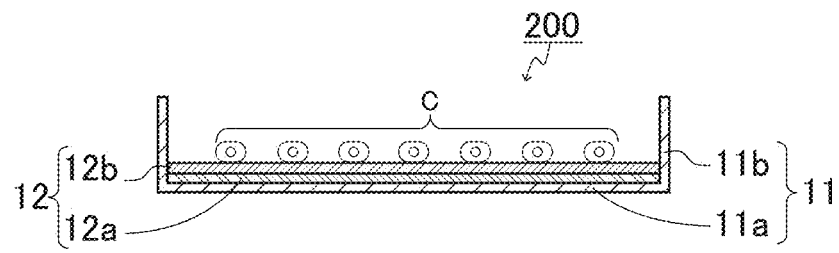
FIGS. 4A-4E are schematic views showing an example of a cell processing method of the second embodiment.
Figure 4B:
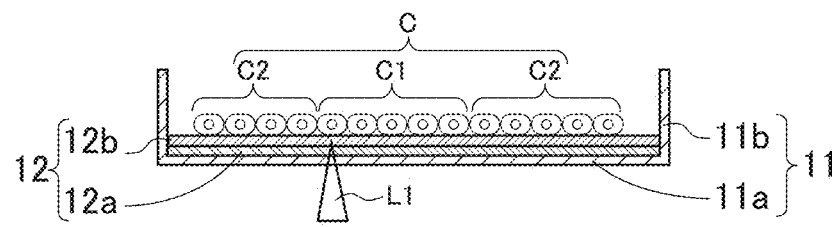

First, in the processing method of the present embodiment, as shown in FIGS. 4A and 4B, cells are cultured in the culture instrument 200 (culturing step). Cells to be cultured can be introduced, for example, by introducing a cell suspension into the culture instrument 200. The culture conditions (culture temperature, culture humidity, gas partial pressure, culture time, and the like) in the culturing step can be appropriately determined according to the type of the cells, for example. Specifically, the culture can be performed in a wet environment at 5% $CO_2$ and 25 to 40° C.

Figure 4C:
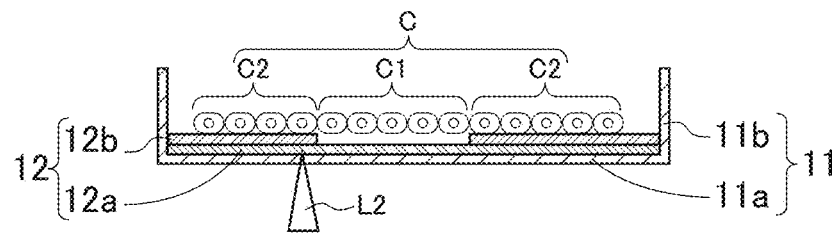

Next, the photosoluble layer 12b is irradiated with first light (L1) that causes photodissolution (first irradiation step). More specifically, in the first irradiation step, the photosoluble layer 12b corresponding to cells C1 to be processed (detached) among cells C is irradiated with L1, that is, the photosoluble layer 12b immediately below the cells C1 to be processed is irradiated with L1. As a result, as shown in FIG. 4C, the photosoluble layer 12b immediately below the cells C1 to be processed is dissolved, and the indirect fixation (adhesion) of the cells C1 to the substrate 11a is released. The wavelength of L1 is a wavelength at which an atomic group responsible for a photosolubility exhibits a photosolubility in the photoreactive polymer. Regarding the specific examples of the wavelength and the light irradiation amount of L1, for example, reference can be made to the description of the first embodiment. While L1 is laser light, i.e., point light in the present embodiment, L1 is not limited thereto and may be planar light.

Figure 4D:
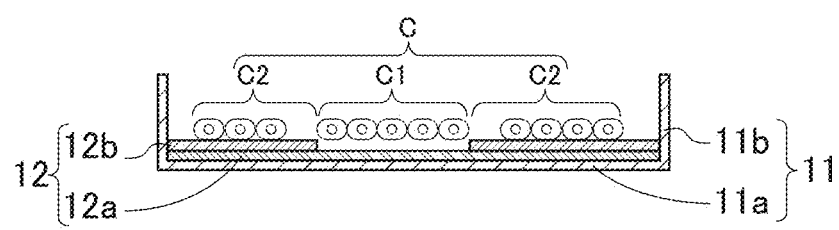
Figure 4E:
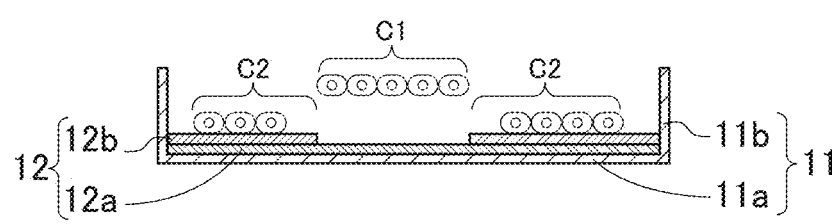

Next, the photothermal convertible layer 12a is irradiated with second light (L2) that causes photothermal conversion (a second irradiation step). Specifically, in the second irradiation step, the photothermal convertible layer 12a corresponding to the boundary between the cells C1 to be processed (detached) and the cells C2 not to be processed (detached) is irradiated with L2, that is, the photothermal convertible layer 12a immediately below the cell C2 adjacent to the cells C1 to be processed among the cells C2 not to be processed is irradiated with L2. As a result, as shown in FIG. 4D, the cell C2 adjacent to the photothermal convertible layer 12a irradiated with L2 is killed, and the fixation between the cells C1 to be processed and the cells C2 not to be processed is released. Thus, as shown in FIG. 4E, the cells C1 to be processed become detachable. The wavelength of L2 is a wavelength at which an atomic group (chromophore) responsible for a photothermal convertibility exhibits a photothermal convertibility in the photoreactive polymer. Regarding the specific examples of the wavelength and the light irradiation amount of L2, for example, reference can be made to the description of the first embodiment. The light irradiation amount of L2 may be, for example, the same as or different from the light irradiation amount of L1 and can be different from the light irradiation amount of L1. Further, the light irradiation amount of L2 can be larger than the light irradiation amount of L1. By setting the light irradiation amount accordingly, the processing method of the present embodiment can effectively kill cells, for example, in the second irradiation step. While L2 is laser light, i.e., point light in the present embodiment, L2 is not limited thereto and may be planar light.

In this manner, the processing method of the present embodiment can detach the cells C1 to be processed.

In the present embodiment, since the second irradiation step is performed after the first irradiation step, the photothermal convertible layer 12a immediately below the cell C2 adjacent to the cells C1 is irradiated with L2. However, the object to be irradiated with L2 is not limited thereto. In other words, in the processing method of the present embodiment, the first irradiation step may be performed after the second irradiation step, or these steps may be performed in parallel. As a specific example, when irradiation of L1 is performed after irradiation of L2, the photothermal convertible layer 12a immediately below the cell C2 adjacent to the cells C1 to be processed or the photothermal convertible layer 12a immediately below the cells C1 adjacent to the cells C2 not to be processed is irradiated with L2 in the second irradiation step, for example. In the first irradiation step, the photosoluble layer 12b immediately below the cells C1 may be irradiated with L1.

While one cell C present at the boundary is killed in the processing method of the present embodiment, a plurality of cells C adjacent to the boundary may be killed. Thereby, the processing method of the present embodiment can effectively prevent, for example, that the cells C1 to be processed remain in the cells C2 not to be processed and that the cells C2 not to be processed are detached together with the cells C1 to be processed.

EXAMPLES

Next, examples will be described. The present invention, however, is not restricted by the following examples. Commercially available reagents were used based on their protocols unless otherwise indicated.

Example 1

A culture instrument was produced and whether cells at a desired position can be detached by a processing method was examined.

(1) Production of Culture Instrument

The culture instrument 100 of the first embodiment was prepared. First, as the photosoluble polymer, a polymer represented by the following formula (11) was synthesized. The polymer of the following formula (11) was synthesized by the same procedure as the compound 12 of WO 2017/013226. Note that the introduction rate of the side chain (2-nitrobenzaldehyde) was 10 mol %. Further, as the photothermal convertible polymer, a polymer of the formula (8) was synthesized.

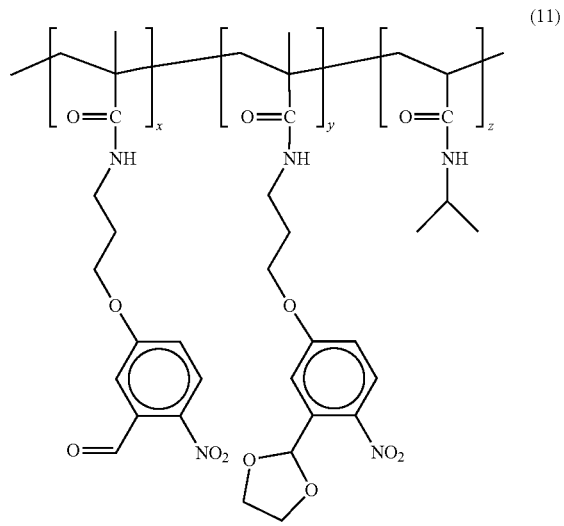

(11)

Next, a 2,2,2-trifluoroethanol (TFE) solution containing 1.0% (w/w) photosoluble polymer and 0.085% (w/w) photothermal convertible polymer was prepared, and the obtained solution was spin-coated on the surface of the substrate 11a made of polystyrene to form the photoreactive layer 12. In this manner, the culture instrument 100 (Example 1) was produced.

Cell Processing

Figure 5A:
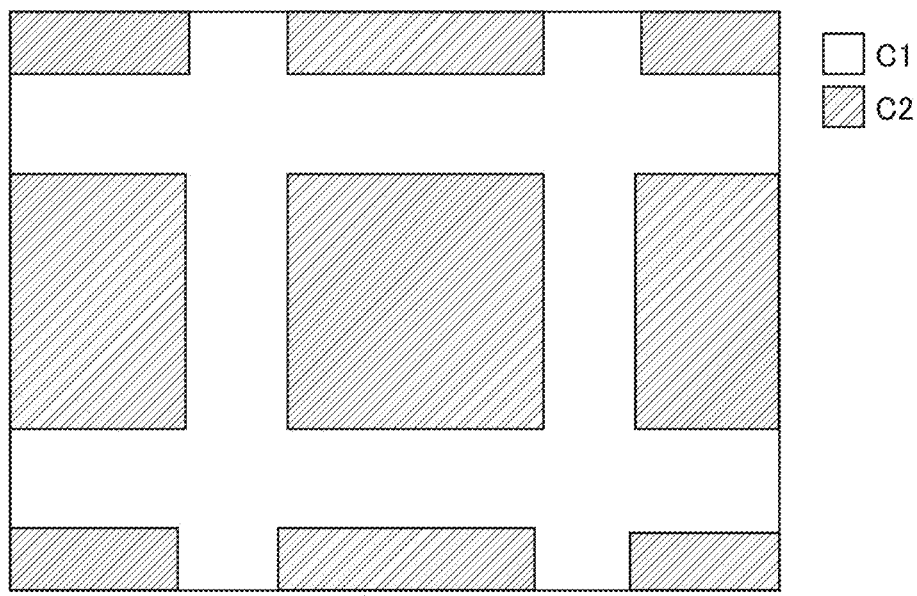
FIGS. 5A and 5B show a region of cells to be processed and the result after processing in Example 1.
Figure 5B:
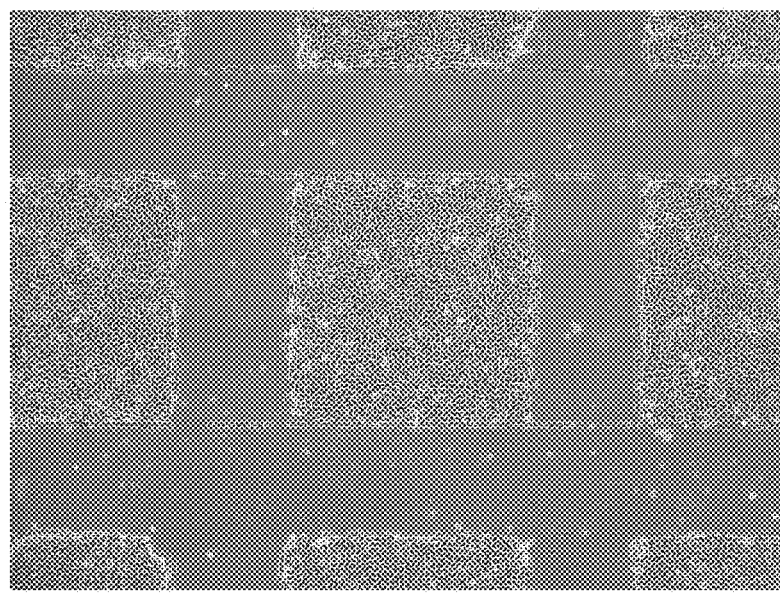

MDCK cells (purchased from Riken BioResource Research Center) were dispersed in a medium and seeded into the culture instrument 100 of Example 1 and cultured for half a day. As the medium for MDCK cells, a MEM medium containing 10% fetal bovine serum (FBS) was used. As to the culture conditions, the culture was performed at 5% $CO_2$ and 37° C., and under a wet condition. After the culturing, the cells were checked to be adhered and extended throughout the surface of the substrate 11a. Then, L1 and L2 were emitted using a cell processing apparatus (produced by Kataoka Corporation) configured to emit lasers from the bottom surface side (lower side in FIG. 1) of the substrate 11a toward the cells C on the photoreactive layer 12. Specifically, as shown in FIG. 5A, the photoreactive layer 12 immediately below the cells C1 to be processed was irradiated with L1. L1 was laser light having a wavelength of 405 nm, a diameter of 25 μm, and an energy intensity of 0.2 W, and scanning was performed in the range of a width of 0.6 mm at 20 μm pitch and a velocity of 1000 mm/s, thereby inducing the dissolution of the photoreactive layer 12. Next, as shown in FIG. 5A, the photoreactive layer 12 immediately below the cell C2 adjacent to the cells C1 among the cells C1 to be processed and the cells C2 not to be processed was irradiated with L2. L2 was laser light having a wavelength of 405 nm, a diameter of 25 μm, and an energy intensity of 0.8 W, and scanning was performed at a velocity of 300 mm/s. Irradiation with L2 was repeated 4 times to induce a cell monolayer to be killed. The culture apparatus 100 was rotated by about 90°, and the irradiation with L1 and L2 was performed in the same manner. After the irradiation, the culture apparatus 100 was stored in an incubator for a while, and then the medium was lightly sprayed onto the surface thereof. As a result, the cells C1 to be processed were detached as shown in FIG. 5B. These results showed that, cells at a desired position can be detached using the culture instrument of the present disclosure by the processing method of the present disclosure.

Example 2

A culture instrument was produced and whether cells at a desired position can be detached by a processing method was examined (1) Production of Culture Instrument A connection layer was provided between the photoreactive layer 12 and the substrate 11a and a cell culture base material layer was laminated on the photoreactive layer 12 in the culture instrument 100 of the first embodiment, thereby preparing a culture instrument. First, as the photosoluble polymer, the polymer of formula (11) synthesized in Example 1 (1) described above was used. Further, as the photothermal convertible polymer, a polymer of the formula (9) was synthesized.

First, a methanol solution containing 0.49% (w/w) hydroxypropylcellulose (MW=100,000), 0.047% (w/w) poly(ethylene glycol)bis(carboxymethyl)ether (MW=600), and 0.49 mol/kg sulfuric acid was prepared, and the obtained solution was spin-coated on the surface of the substrate 11a made of polystyrene. Next, the obtained culture instrument was heated at 85° C. for 18 hours, washed with ethanol, and then dried.

After the drying, a TFE solution containing 1.9% (w/w) photosoluble polymer and 0.088% (w/w) photothermal convertible polymer was prepared, and the obtained solution was spin-coated on the surface of the substrate 11a made of polystyrene. After the spin coating, the resultant was irradiated with ultraviolet light having a wavelength of 365 nm and an energy density of 0.9 mW/cm$^2$ for 15 seconds, thereby forming the photoreactive layer 12.

Next, using a diluted solution obtained by diluting 9.6 μL of iMatrix511 (produced by Nippi. Inc.) into 2 mL of PBS, a cell culture base material layer was formed in the culture instrument having the photoreactive layer 12 according to the attached protocol. In this manner, a culture instrument (Example 2) was produced.

(2) Cell Processing

Figure 6A:
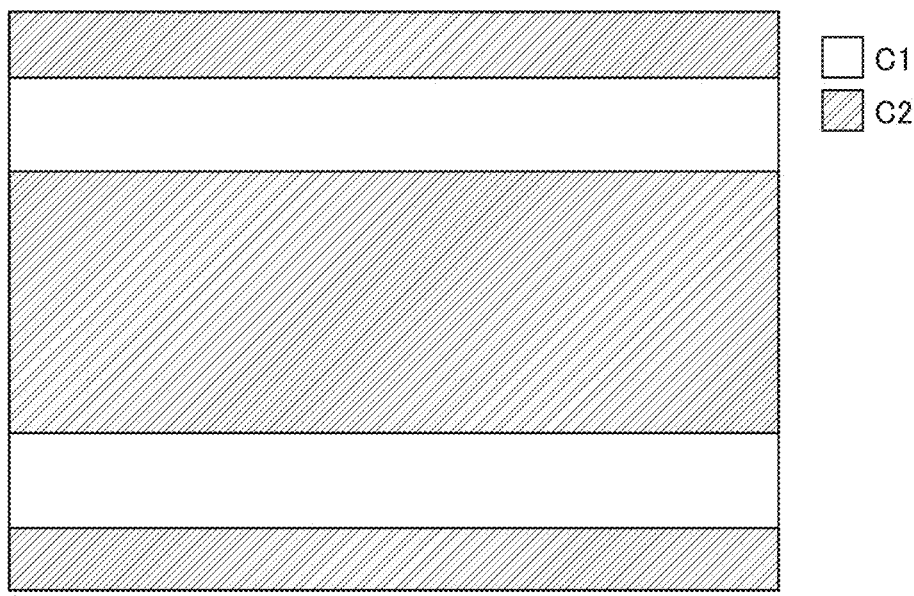
FIGS. 6A and 6B show a region of cells to be processed and the result after processing in Example 2.
Figure 6B:
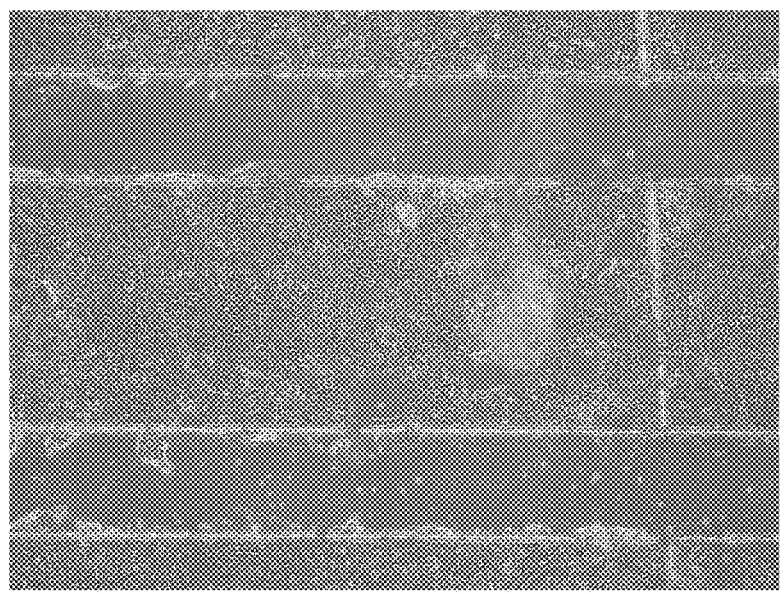

Human iPS cells (201B7 line, purchased from Riken BioResource Center) suspended in the medium were seeded into the culture instrument of Example 2 and cultured for 5 days. As a medium for the iPS cells, StemFitAK02N (Ajinomoto Co., Inc.) was used. As to the culture conditions, the culture was performed at 5% $CO_2$ and 37° C., and under a wet condition. After the culturing, the cells were checked to be adhered and extended throughout the surface of the substrate 11a. Then, L1 and L2 were emitted using the cell processing apparatus from the bottom surface side (lower side in FIG. 1) of the substrate 11a toward the cells C on the photoreactive layer 12. Specifically, as shown in FIG. 6A, the photoreactive layer 12 immediately below the cells C1 to be processed was irradiated with L1. L1 was laser light having a wavelength of 405 nm, a diameter of 25 μm, and an energy intensity of 0.2 W or 0.3 W, and scanning was performed once (in the case of 0.3 W) or twice (in the case of 0.2 W) in the range of a width of 0.6 mm at 10 μm pitch and a velocity of 1000 mm/s, thereby inducing the dissolution of the photoreactive layer 12. Next, as shown in FIG. 6A, the photoreactive layer 12 immediately below the cell C2 adjacent to the cells C1 among the cells C1 to be processed and the cells C2 not to be processed was irradiated with L2. L2 was laser light having a wavelength of 405 nm, a diameter of 25 μm, and an energy intensity of 0.8 W, and scanning was performed at a velocity of 200 mm/s to induce a cell monolayer to be killed. After the irradiation, the culture apparatus 100 was stored in an incubator for a while, and then the medium was lightly sprayed onto the surface thereof. As a result, the cells C1 to be processed were detached as shown in FIG. 6B. While FIG. 6B is a photograph in the case where L1 was 0.2 W, the detachment of the cells C1 to be processed was observed also in the case where L1 was 0.3 W. These results showed that, cells at a desired position can be detached using the culture instrument of the present disclosure by the processing method of the present disclosure.

Example 3

A culture instrument was produced and whether cells at a desired position can be detached by a processing method was examined (1) Production of Culture Instrument The culture instrument 100 of the first embodiment was prepared. First, as the photosoluble polymer, a polymer represented by the following formula (12) was synthesized. Further, as the photoreactive polymer (a polymer having a photosolubility and a photothermal convertibility), a polymer of the following formula (13) was synthesized using the polymer of the formula (12). The polymer of the formula (12) was synthesized by the same procedure as the synthetic procedure of the compound 12 of WO 2017/013226 except that N-tert-butylacrylamide was used instead of N-isopropylacrylamide. Note that the introduction rate of the side chain (2-nitrobenzaldehyde) was 19 mol %. Next, to a TFE solution containing the polymer of the formula (12) having a concentration of 1.8% (w/w), Disperse Orange 3 was added so as to achieve the concentration of 0.016% (w/w) and then stirred. As a result, the aldehyde group of the polymer of the formula (12) and the amino group of the Disperse Orange 3 reacted with each other, and the color of the solution changed from orange to purple, thereby synthesizing a polymer of the formula (13).

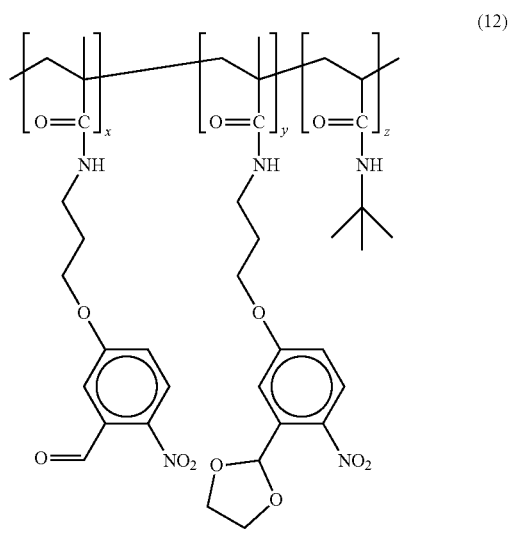

(12)

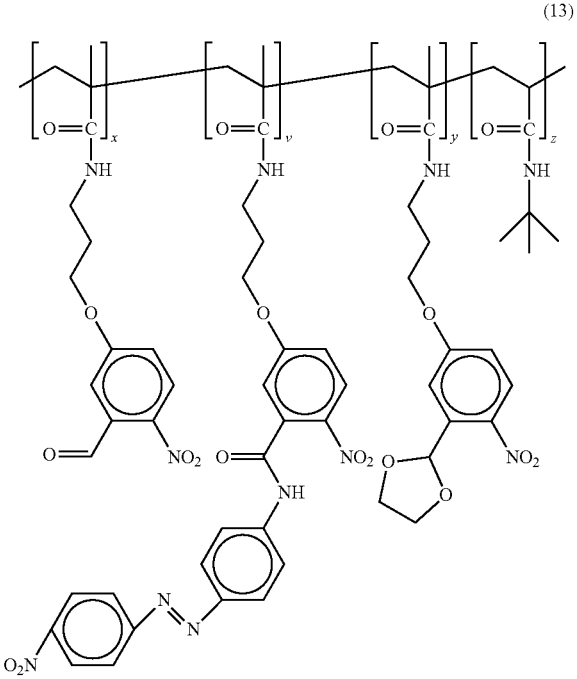

(13)

Next, the obtained solution was spin-coated on the surface of the substrate 11a made of polystyrene to form the photoreactive layer 12. In this manner, a culture instrument 100 (Example 3-1) was produced.

Further, using a diluted solution obtained by diluting 0.2 µL of iMatrix511 (produced by Nippi. Inc.) into 1.5 mL of PBS, a cell culture base material layer was formed in the culture instrument 100 of Example 3-1 according to the attached protocol. In this manner, a culture instrument (Example 3-2) was produced.

(2) Cell Processing 1

Figure 7A:
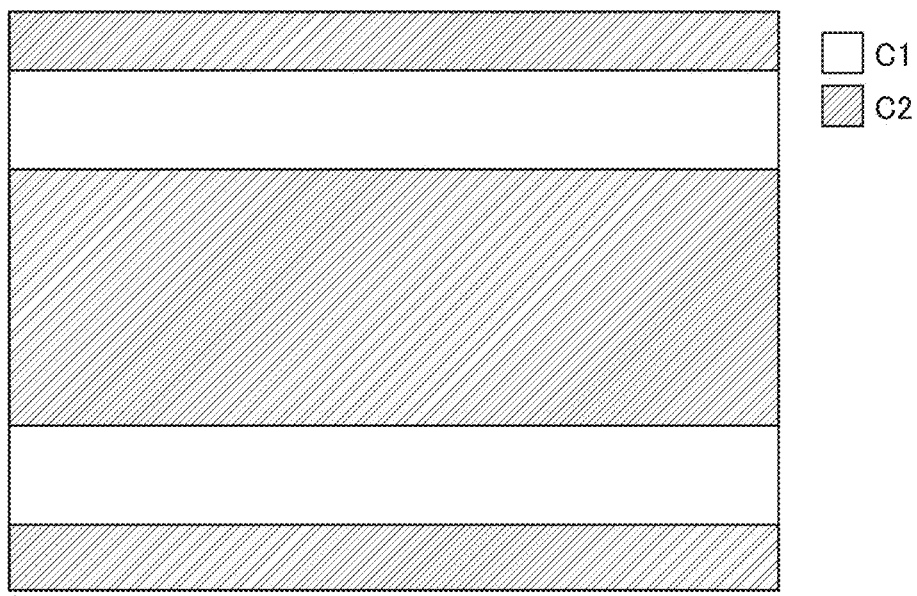
FIGS. 7A and 7B show a region of cells to be processed and the result after processing in Example 3.
Figure 7B:
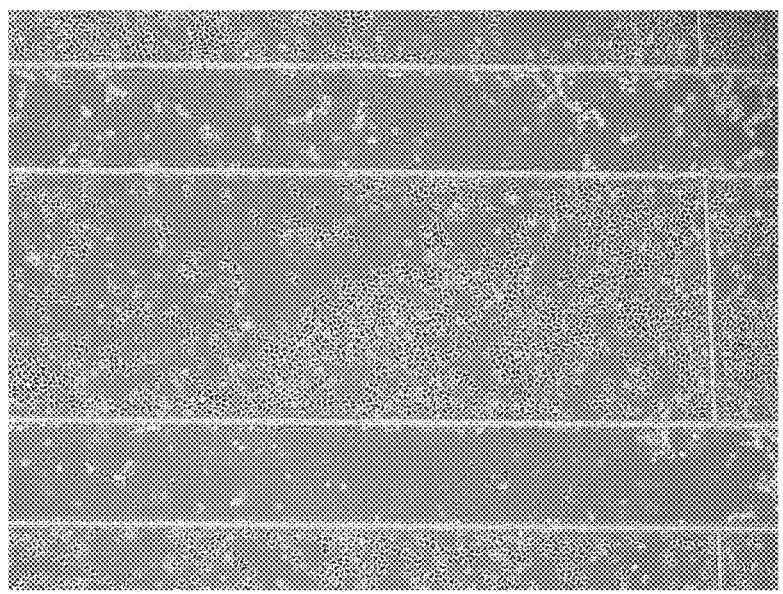

HeLa cells (purchased from Riken BioResource Research Center) were dispersed in a medium and seeded into the culture instrument 100 of Example 3-1 and cultured for half a day. As the medium for HeLa cells, a MEM medium containing 10% FBS was used. As to the culture conditions, the culture was performed at 5% $CO_2$ and 37° C., and under a wet condition. After the culturing, the cells were checked to be adhered and extended throughout the surface of the substrate 11a. Then, L1 and L2 were emitted using the cell processing apparatus from the bottom surface side (lower side in FIG. 1) of the substrate 11a toward the cells C on the photoreactive layer 12. Specifically, as shown in FIG. 7A, the photoreactive layer 12 immediately below the cells C1 to be processed was irradiated with L1. L1 was laser light having a wavelength of 405 nm, a diameter of 25 µm, and an energy intensity of 0.2 W or 0.3 W, and scanning was performed in the range of a width of 0.6 mm at 10 µm pitch and a velocity of 1000 mm/s, thereby inducing the dissolution of the photoreactive layer 12. Next, as shown in FIG. 7A, the photoreactive layer 12 immediately below the cell C2 adjacent to the cells C1 among the cells C1 to be processed and the cells C2 not to be processed was irradiated with L2. L2 was laser light having a wavelength of 405 nm, a diameter of 25 µm, and an energy intensity of 0.8 W, and scanning was performed at a velocity of 200 mm/s to induce a cell monolayer to be killed. After the irradiation, the culture apparatus 100 was stored in an incubator for a while, and then the medium was lightly sprayed onto the surface thereof. As a result, the cells C1 to be processed were detached as shown in FIG. 7B. While FIG. 7B is a photograph in the case where L1 was 0.2 W, the detachment of the cell C1 to be processed was observed also in the case where L1 was 0.3 W.

(3) Cell Processing 2

Figure 8A:
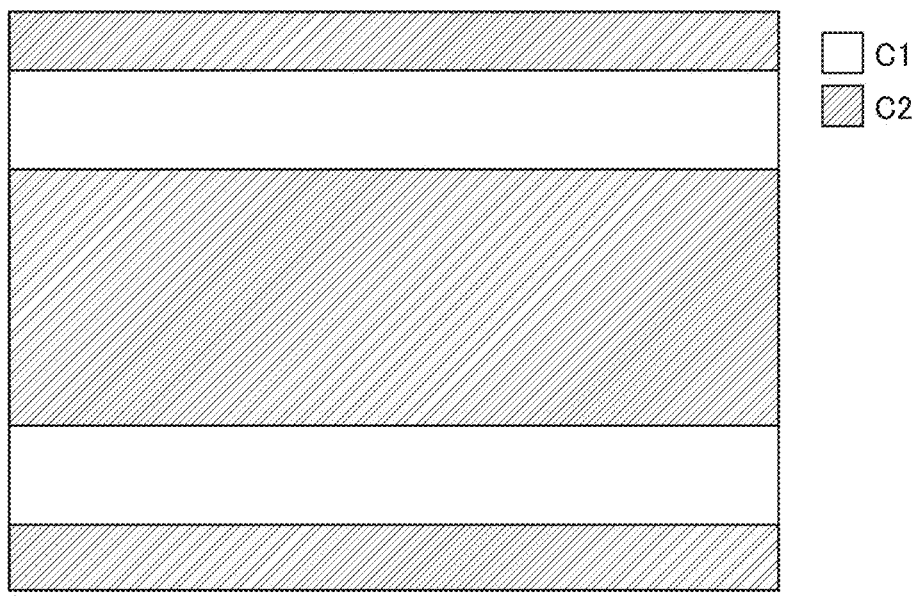
FIGS. 8A and 8B show a region of cells to be processed and the result after processing in Example 3.
Figure 8B:
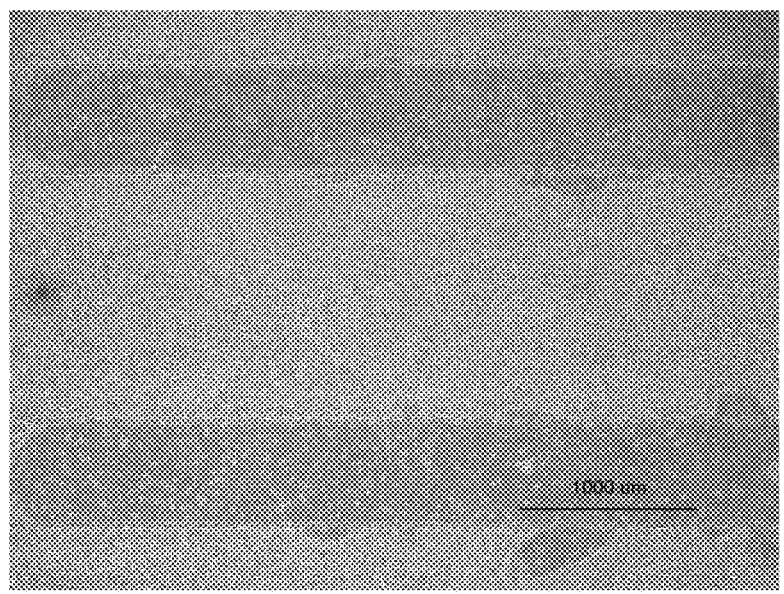

The human iPS cells suspended in a medium were seeded into the culture instrument 100 of Example 3-2 and cultured under the same conditions as in Example 2 for 5 days. After the culturing, the cells were checked to be adhered and extended throughout the surface of the substrate 11a. Then, L1 and L2 were emitted using the cell processing apparatus from the bottom surface side (lower side in FIG. 1) of the substrate 11a toward the cells C on the photoreactive layer 12. Specifically, as shown in FIG. 8A, the photoreactive layer 12 immediately below the cells C1 to be processed was irradiated with L1. L1 was laser light having a wavelength of 405 nm, a diameter of 25 µm, and an energy intensity of 0.2 W or 0.3 W, and scanning was performed in the range of a width of 0.6 mm at 10 µm pitch and a velocity of 1000 mm/s, thereby inducing the dissolution of the photoreactive layer 12. Next, as shown in FIG. 8A, the photoreactive layer 12 immediately below the cell C2 adjacent to the cells C1 among the cells C1 to be processed and the cells C2 not to be processed was irradiated with L2. L2 was laser light having a wavelength of 405 nm, a diameter of 25 µm, and an energy intensity of 0.8 W, and scanning was performed at a velocity of 200 mm/s to induce a cell monolayer to be killed. After the irradiation, the culture apparatus 100 was stored in an incubator for a while, and then the medium was lightly sprayed onto the surface thereof. As a result, the cells C1 to be processed were detached as shown in FIG. 8B. While FIG. 8B is a photograph in the case where L1 was 0.2 W, the detachment of the cells C1 to be processed was observed also in the case where L1 was 0.3 W. These results showed that, cells at a desired position can be detached using the culture instrument of the present disclosure by the processing method of the present disclosure.

These results showed that, cells at a desired position can be detached using the culture instrument of the present disclosure by the processing method of the present disclosure.

Example 4

A culture instrument was produced and whether cells at a desired position can be detached by a processing method was examined (1) Production of Culture Instrument The culture instrument 200 of the second embodiment was prepared. First, as the photothermal convertible polymer, the polymer of the formula (10) was synthesized. Specifically, 0.0035 g of 4-(4-nitrophenylazo)phenol and 0.008 g poly(glycidyl methacrylate) were dissolved in 0.457 g of acetone. To the obtained solution, 0.0086 g of 1,2-dichloroethane solution containing 2.8% (w/w) diazabicycloundecene (DBU) was added, and then stirred and reacted at 60° C. for 5 days. As a result, the color was changed from orange to deep red. This demonstrated that 4-(4-nitrophenylazo)phenol was introduced into the glycidyl group of poly(glycidyl methacrylate) and the polymer of the formula (10) was synthesized. As the photosoluble polymer, the polymer of the formula (12) synthesized in Example 3 (1) was used.

From the polymer solution of the formula (10), 0.164 g of the solution was fractionated and acetone was removed by nitrogen spraying, and the resultant was redissolved in 0.0478 g of TFE. Further, to the obtained solution, 0.0041 g of a TFE solution containing 0.05% (w/w) 1,12-diaminododecane was added, and then stirred. Next, the obtained solution was spin-coated on the surface of the substrate 11a made of polystyrene, and then heated at 85° C. for 4 hours, and further washed with ethanol and re-dried to form the photothermal convertible layer 12a. Next, a TFE solution containing the polymer of the formula (12) having a concentration of 1.8% (w/w) was spin-coated on the surface of the photothermal convertible layer 12a, and then irradiated with ultraviolet light having a wavelength of 365 nm and an energy intensity of 1.5 mW/cm$^2$ for 4 seconds, thereby producing the culture instrument 200.

(2) Cell Processing

Figure 9A:
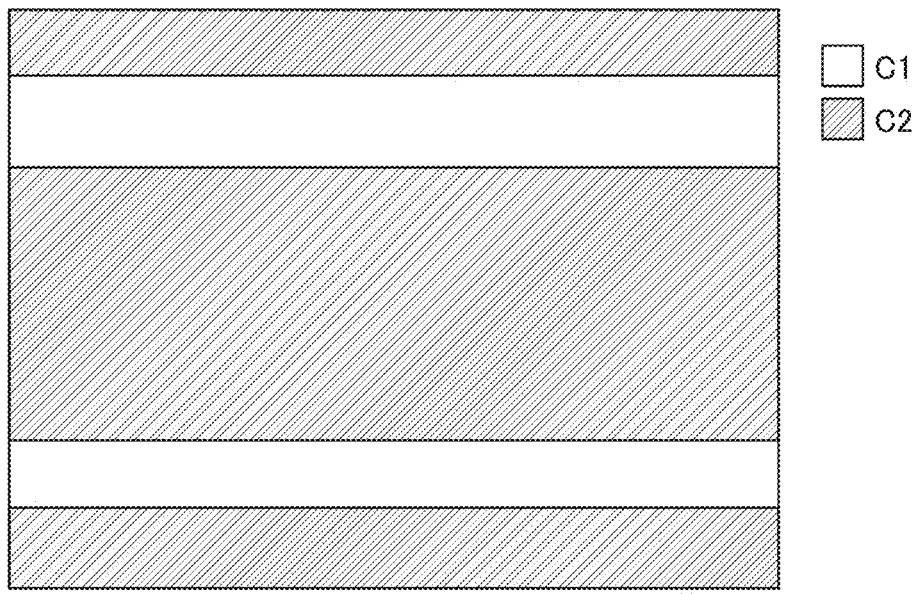
FIGS. 9A and 9B show a region of cells to be processed and the result after processing in Example 4.
Figure 9B:
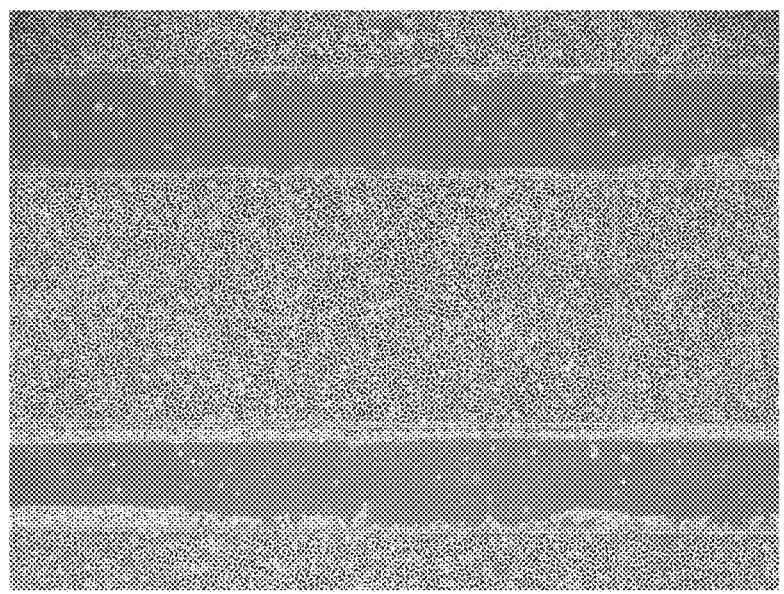

HeLa cells were dispersed in a medium and seeded into the culture instrument 200 of Example 4 and cultured for half a day. As the medium for HeLa cells, a MEM medium containing 10% FBS was used. As to the culture conditions, the culture was performed at 5% $CO_2$ and 37° C., and under a wet condition. After the culturing, the cells were checked to be adhered and extended throughout the surface of the substrate 11a. Then, L1 and L2 were emitted using the cell processing apparatus from the bottom surface side (lower side in FIG. 3) of the substrate 11a toward the cells C on the photoreactive layer 12. Specifically, as shown in FIG. 9A, the photoreactive layer 12 immediately below the cells C1 to be processed was irradiated with L1. L1 was laser light having a wavelength of 405 nm, a diameter of 25 µm, and an energy intensity of 0.2 W or 0.3 W, and scanning was performed in the range of a width of 0.6 mm at 10 µm pitch and a velocity of 1000 mm/s, thereby inducing the dissolution of the photoreactive layer 12. Next, as shown in FIG. 9A, the photoreactive layer 12 immediately below the cell C2 adjacent to the cells C1 among the cells C1 to be processed and the cells C2 not to be processed was irradiated with L2. L2 was laser light having a wavelength of 405 nm, a diameter of 25 µm, and an energy intensity of 0.8 W, and scanning was performed twice at a velocity of 750 mm/s to induce a cell monolayer to be killed. After the irradiation, the culture apparatus 200 was stored in an incubator for a while, and then the medium was lightly sprayed onto the surface thereof. As a result, the cells C1 to be processed were detached as shown in FIG. 9B. While FIG. 9B is a photograph in the case where L1 was 0.2 W, the detachment of the cells C1 to be processed was observed also in the case where L1 was 0.3 W. These results showed that, cells at a desired position can be detached using the culture instrument of the present invention by the processing method of the present invention.

Accordingly, cells at a desired position can be detached. For this reason, the cell culture instruments and cell processing methods are extremely useful in a life science field, a medical field, or the like, which performs processing of cells, tissues, and the like.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A cell culture instrument, comprising:
   a substrate; and
   a photoreactive layer having a photosolubility and a photothermal convertibility, wherein
   the photoreactive layer is laminated on the substrate,
   the photoreactive layer comprises a polymer having a photosolubility and a photothermal convertibility;
   the photoreactive layer comprises a photosoluble layer having a photosolubility and a photothermal convertible layer having a photothermal convertibility,
   the photosoluble layer comprises a photosoluble polymer, and
   the photothermal convertible layer comprises a photothermal convertible polymer.

2. The cell culture instrument according to claim 1, wherein
   the photosoluble polymer has a main chain and a side chain,
   the side chain has an aromatic ring,
   the aromatic ring includes a first carbon atom substituted with a nitro group and a second carbon atom substituted with an aldehyde group or a functional group represented by the following formula (1), and
   the first carbon atom and the second carbon atom are adjacent to each other within the same benzene ring.

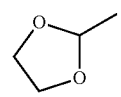

(1)

3. The cell culture instrument according to claim 2, wherein
   the photosoluble polymer includes a polymer represented by the following formula (2):

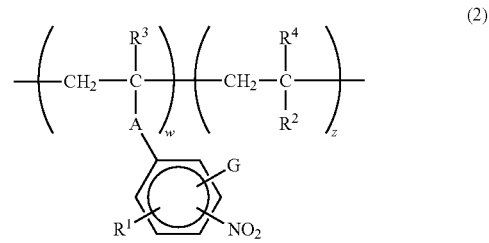

(2)

where in the formula (2),

A is a single bond or a functional group, $R^1$ is an aldehyde group or a functional group represented by the formula (1), $R^1$ and $NO_2$ are each attached to adjacent carbon atoms, $R^2$ is at least one selected from the group consisting of hydrogen atoms, alkyl groups, functional groups represented by the following formula (3), and functional groups represented by the following formula (4), $R^3$ and $R^4$ may be the same or different and are each independently a hydrogen atom or an alkyl group, G is three or less alkyl groups which may be substituted with hydrogen in a benzene ring, and w and z represent mole percentages and satisfy $0<w\leq100$ and $0\leq z<100$, respectively

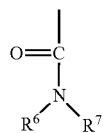
(3)

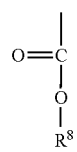
(4)

where in the formula (3), $R^6$ and $R^7$ may be the same or different and are each independently a hydrogen atom, an alkyl group, or an aromatic ring, and where in the formula (4), $R^8$ is an alkyl group.

4. The cell culture instrument according to claim 2, wherein
the photosoluble polymer comprises a polymer represented by the following formula (5):

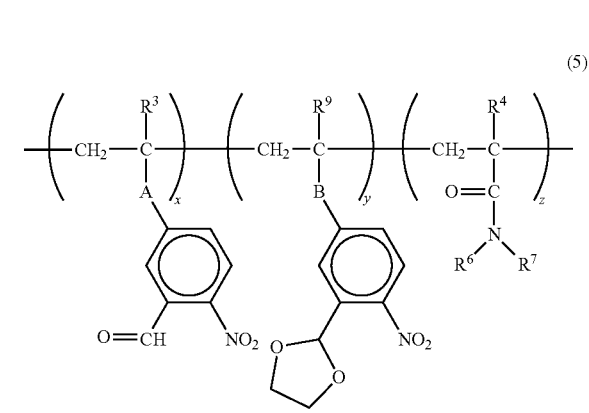
(5)

where in the formula (5),

A and B may be the same or different and are each independently a single bond or a functional group, $R^3$, $R^4$, and $R^9$ may be the same or different and are each independently a hydrogen atom or an alkyl group, $R^6$ and $R^7$ may be the same or different and are each independently a hydrogen atom, an alkyl group, or an aromatic ring, and x, y, and z represent mole percentages and satisfy $0\leq x<100$, $0\leq y<100$, and $0\leq z<100$ (except for x=y=0), respectively.

5. The cell culture instrument according to claim 1, wherein
the photothermal convertible polymer has a main chain and a side chain, and
the side chain has a chromophore having a predetermined absorbance at a wavelength of 350 nm or more.

6. The cell culture instrument according to claim 5, wherein the chromophore has an azobenzene skeleton.

7. A cell culture instrument, comprising:
a substrate; and
a photoreactive layer having a photosolubility and a photothermal convertibility, wherein
the photoreactive layer is laminated on the substrate,
the photoreactive layer comprises a polymer having a photosolubility and a photothermal convertibility; and
the polymer having a photosolubility and a photothermal convertibility is represented by the following formula (6):

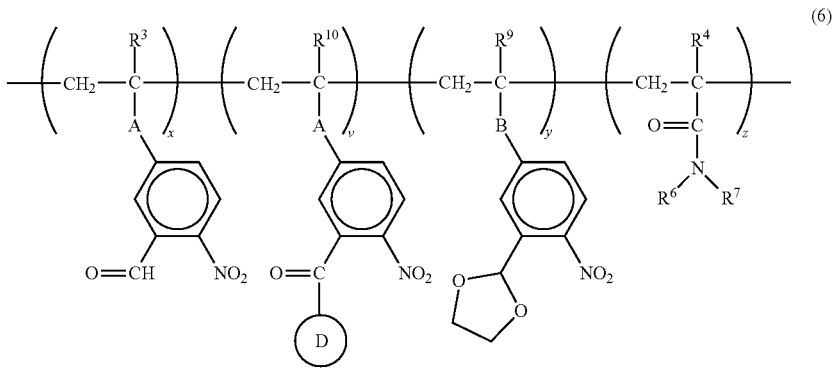
(6)

where in the formula (6),

A and B may be the same or different and are each independently a single bond or a functional group, $R^3$, $R^4$, $R^9$, and $R^{10}$ may be the same or different and are each independently a hydrogen atom or an alkyl group, $R^6$ and $R^7$ may be the same or different and are each independently a hydrogen atom, an alkyl group, or an aromatic ring, D is a chromophore having a predetermined absorbance at a wavelength of 350 nm or more, and v, x, y, and z represent mole percentages and satisfy $0<v<100$, $0\leq x<100$, $0\leq y<100$, and $0\leq z<100$ (except for x=y=0), respectively.

8. A cell culture instrument, comprising:
a substrate; and
a photoreactive layer having a photosolubility and a photothermal convertibility, wherein
the photoreactive layer is laminated on the substrate,
the photoreactive layer comprises a polymer having a photosolubility and a photothermal convertibility; and
the polymer having a photosolubility and a photothermal convertibility is represented by the following formula (7):

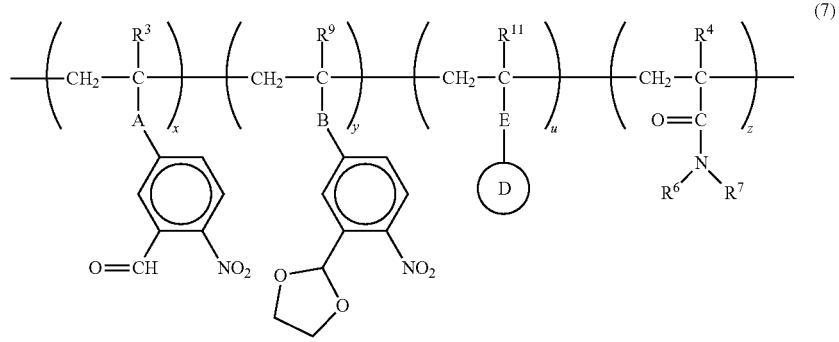

(7)

where in the formula (7),

A, B, and E may be the same or different and are each independently a single bond or a functional group, $R^3$, $R^4$, $R^9$, and $R^{11}$ may be the same or different and are each independently a hydrogen atom or an alkyl group, $R^6$ and $R^7$ may be the same or different and are each independently a hydrogen atom, an alkyl group, or an aromatic ring, D is a chromophore having a predetermined absorbance at a wavelength of 350 nm or more, and u, x, y, and z represent mole percentages and satisfy $0<u<100$, $0\leq x<100$, $0\leq y<100$, and $0\leq z<100$ (except for x=y=0), respectively.

9. The cell culture instrument according to claim 8, comprising:
a connection layer connecting the photoreactive layer and the substrate, wherein
the connection layer is laminated on the substrate, and
the photoreactive layer is laminated on the connection layer.

10. The cell culture instrument according claim 8, wherein cells are cultured on the photoreactive layer.

11. A cell processing method, comprising:
providing a cell culture instrument comprising:
a substrate; and
a photoreactive layer having a photosolubility and a photothermal convertibility,
wherein the photoreactive layer is laminated on the substrate, and
the photoreactive layer comprises a polymer having a photosolubility and a photothermal convertibility;
culturing cells in the cell culture instrument;
irradiating the photoreactive layer with first light that causes photodissolution; and
irradiating the photoreactive layer with second light that causes photothermal conversion.

12. The cell processing method according to claim 11, wherein
in the irradiating of the photoreactive layer with first light, a photoreactive layer corresponding to cells to be processed among the cells is irradiated with the first light, and
in the irradiating of the photoreactive layer with second light, a photoreactive layer corresponding to a boundary between the cells to be processed and cells not to be processed among the cells is irradiated with the second light.

13. The cell processing method according to claim 11, wherein
in the irradiating of the photoreactive layer with second light, a cell corresponding to the photoreactive layer irradiated with the second light is killed.

14. The cell processing method according to claim 11, wherein the light irradiation amount of the second light is larger than the light irradiation amount of the first light.

15. The cell culture instrument according to claim 1, comprising:
a connection layer connecting the photoreactive layer and the substrate, wherein
the connection layer is laminated on the substrate, and
the photoreactive layer is laminated on the connection layer.

16. The cell culture instrument according claim 1, wherein cells are cultured on the photoreactive layer.

17. The cell culture instrument according to claim 7, comprising:
a connection layer connecting the photoreactive layer and the substrate, wherein
the connection layer is laminated on the substrate, and
the photoreactive layer is laminated on the connection layer.

18. The cell culture instrument according claim 7, wherein cells are cultured on the photoreactive layer.

* * * * *